(12) United States Patent
Jalde

(10) Patent No.: US 12,257,386 B2
(45) Date of Patent: Mar. 25, 2025

(54) SYSTEM FOR DETECTION OF LEAKAGE OR ABNORMAL RESISTANCE IN A VENTILATION SYSTEM

(71) Applicant: MAQUET CRITICAL CARE AB, Solna (SE)

(72) Inventor: Fredrik Jalde, Sundbyberg (SE)

(73) Assignee: MAQUET CRITICAL CARE AB, Solna (SE)

( * ) Notice: Subject to any disclaimer, the term of this patent is extended or adjusted under 35 U.S.C. 154(b) by 1348 days.

(21) Appl. No.: 16/487,019

(22) PCT Filed: Mar. 1, 2017

(86) PCT No.: PCT/SE2017/050189
§ 371 (c)(1),
(2) Date: Aug. 19, 2019

(87) PCT Pub. No.: WO2018/160107
PCT Pub. Date: Sep. 7, 2018

(65) Prior Publication Data
US 2021/0128852 A1    May 6, 2021

(51) Int. Cl.
*A61M 16/00* (2006.01)
*A61M 16/10* (2006.01)

(52) U.S. Cl.
CPC ...... *A61M 16/024* (2017.08); *A61M 16/0051* (2013.01); *A61M 16/0057* (2013.01);
(Continued)

(58) Field of Classification Search
CPC ............ A61M 16/024; A61M 16/0051; A61M 16/10; A61M 2016/0015;
(Continued)

(56) References Cited

U.S. PATENT DOCUMENTS

2016/0228661 A1* 8/2016 Larsson ................. A61B 5/389
2017/0182267 A1* 6/2017 Cameron ............. A61M 11/042

FOREIGN PATENT DOCUMENTS

| WO | 00/76389 | 12/2000 | |
| WO | 02/056818 | 7/2002 | |
| WO | WO-2016153406 A1 * | 9/2016 | ........... A61B 5/0803 |

OTHER PUBLICATIONS

Definition of "establish", https://www.oxfordlearnersdictionaries.com/us/definition/english/establish, Accessed on May 16, 2023. (Year: 2023).*

* cited by examiner

*Primary Examiner* — Kendra D Carter
*Assistant Examiner* — Maap Ahmed Ellabib
(74) *Attorney, Agent, or Firm* — Fay Kaplun & Marcin, LLP

(57) ABSTRACT

A system is for detection of leakage or abnormal resistance in a ventilation system. The ventilation system includes a breathing apparatus which provides a mechanical ventilation to a patient. The system includes a bioelectric sensor arrangement detecting a bioelectric signal indicative of the patient's effort to breathe and a control computer configured to receive the bioelectric signal detected by the bioelectric sensor arrangement. The control computer is further configured to determine a change in the bioelectric signal and to establish leakage or abnormal resistance in the ventilation system based on the change in the bioelectric signal.

21 Claims, 4 Drawing Sheets

(52) U.S. Cl.
CPC ..... *A61M 16/10* (2013.01); *A61M 2016/0015* (2013.01); *A61M 2016/0018* (2013.01); *A61M 2205/15* (2013.01); *A61M 2205/18* (2013.01); *A61M 2210/1014* (2013.01); *A61M 2230/005* (2013.01); *A61M 2230/08* (2013.01); *A61M 2230/40* (2013.01)

(58) Field of Classification Search
CPC ...... A61M 2016/0018; A61M 2205/15; A61M 2205/18; A61M 2210/1014; A61M 2230/005; A61M 2230/08; A61M 2230/40; A61M 2230/60
See application file for complete search history.

SYSTEM FOR DETECTION OF LEAKAGE OR ABNORMAL RESISTANCE IN A VENTILATION SYSTEM

TECHNICAL FIELD

The present invention pertains to the field of mechanical ventilation and, in particular, to a method, system and computer program for detection of leakage or abnormal resistance in a ventilation system comprising a breathing apparatus providing mechanical ventilation to a patient.

BACKGROUND

All ventilation systems exhibit a certain extent of leakage during administration of pressurized breathing gas. Leakage renders determination of the breathing gas pressure and flow actually reaching the airways of the patient difficult, thus making it hard to establish whether or not the patient receives adequate ventilation.

In particular, considerable leakage may occur in the patient interface during non-invasive ventilation (NIV), i.e., when the patient is not intubated and the patient is connected to the breathing apparatus by means of a face mask, prongs, or any other type of non-invasive patient connector.

Leakage may suddenly occur or increase during ongoing NIV ventilation due to disconnection or movement of the patient connector, typically caused by patient movements. To avoid such patient critical situations, there is a desire to continuously monitor leakage in ventilation systems, and in particular in ventilation systems that may provide NIV ventilation.

Several systems exist that monitors leakage in ventilation systems by continuously calculating leakage from flow and pressure measurements obtained in the gas flow path connecting the breathing apparatus with the patient. However, it is difficult to accurately determine leakage from flow and pressure measurements, in particular during NIV ventilation of paediatric patients where leakage and flow resistance in the patient interface often are considerable. Furthermore, even if the leakage can be estimated, it is often difficult to determine during which part of the breathing cycle the leakage occurs, and, thus, it is difficult to determine the impact of the leakage on the ongoing ventilatory treatment of the patient.

Furthermore, known methods for leakage detection typically require both inspiratory and expiratory flows and/or pressures to be measured and can hence only be performed by ventilation systems having a certain sensor setup. For example, known ventilation systems lacking the ability to measure expiratory flows and/or pressures cannot reliably detect leakage, and even less reliably identify the part of the breathing cycle during which leakage occurs.

SUMMARY

The present invention relates to detecting leakage or abnormal resistance in a ventilation system, such as may be applied to ventilation systems providing NIV ventilation. In this context, leakage pertains to loss of pressurized breathing gas from the ventilation system and abnormal resistance pertains to an increased resistance to gas flow within the system, such as may occur due to partial or complete blockage of gas flow through gas conduits due to bodily fluids and the like.

In addition, the present invention relates to a detection system for detection of leakage or abnormal resistance in a ventilation system, which detection system does not require a certain sensor setup for pressure and/or flow measurements. In other words, it is an object of this disclosure to provide a detection system that is not limited to a particular sensor configuration.

Furthermore, the present invention relates to a method and system for detection of leakage or abnormal resistance in a ventilation system during non-invasive ventilation of paediatric patients.

This disclosure is based on the realization that the respiratory drive of the patient, i.e., the patient's effort to breathe, can be used as an indication of unexpected leakage or abnormal resistance in the ventilation system. In particular, changes in the respiratory drive of the patient following a change in the level of ventilatory assist, provided by a breathing apparatus for mechanically ventilating the patient, may be advantageously used to detect a leakage or abnormal resistance in the ventilation system.

An advantage of detecting leakage and abnormal resistance based on changes in the respiratory drive of the patient is that a bioelectric signal indicative of the respiratory drive of the patient can be used instead of pressure and flow measurements obtained by various sensors in the ventilation system. For example, an Edi signal representing the electrical activity of the diaphragm of the patient may be used for leakage detection. Such a signal is often readily available at the bedside of patients undergoing mechanical ventilation, in particular during Neurally Adjusted Ventilatory Assist (NAVA) ventilation where the Edi signal is used to control the ventilation of the patient.

According to one aspect of the present disclosure, there is provided a method for detection of leakage or abnormal resistance in a ventilation system comprising a breathing apparatus providing mechanical ventilation to a patient. The method comprises the steps of:
  measuring a bioelectric signal indicative of the patient's effort to breathe;
  determining a change in the bioelectric signal, and
  establishing leakage or abnormal resistance in the ventilation system based on the change in the bioelectric signal.

According to another aspect of the present disclosure, there is provided a detection system for detection of leakage or abnormal resistance in a ventilation system comprising a breathing apparatus providing mechanical ventilation to a patient. The detection system comprises a bioelectric sensor arrangement for detecting a bioelectric signal indicative of the patient's effort to breathe, and a control computer configured to receive the bioelectric signal detected by the bioelectric sensor arrangement. The control computer is further configured to:
  determine a change in the bioelectric signal, and
  establish leakage or abnormal resistance in the ventilation system based on the change in the bioelectric signal.

In some embodiments, the method may comprise the steps of ventilating the patient at a substantially constant level of ventilatory assist and establishing leakage or abnormal resistance in the ventilation system based on a change in the bioelectric signal occurring at the substantially constant level of ventilatory assist. An increase in the bioelectric signal (indicating an increase in the effort to breathe by the patient) that is not occasioned by a change in the level of ventilatory assist is likely to be caused by leakage or abnormal resistance in the ventilation system. Consequently, the method typically comprises the step of determining when the change in the bioelectric signal is indicative of an increase in the effort to breathe by the patient, and, when it is, establishing leakage or abnormal resistance in the ventilation system.

The proposed detection of leakage or abnormal resistance in the ventilation system based on changes in a bioelectric signal indicative of the patient's effort to breathe, measured during ventilation of the patient at a substantially constant level of ventilatory assist, is advantageous in that it provides for quick detection of leakage or abnormal resistance in the ventilation system without affecting the ongoing ventilatory treatment of the patient.

In other embodiments, the method comprises the steps of:
measuring a bioelectric signal indicative of the patient's effort to breathe;
changing a level of ventilatory assist provided to the patient by the breathing apparatus from a first level of ventilatory assist to a second and substantially different level of ventilatory assist;
determining a response in the bioelectric signal to the change in level of ventilatory assist, and
establishing leakage or abnormal resistance in the ventilation system based on the response in the bioelectric signal.

Correspondingly, the control computer of the detection system may be configured to:
determine a response in the bioelectric signal to a change in a level of ventilatory assist from a first level of ventilatory assist to a second and substantially different level of ventilatory assist, which ventilatory assist is provided to the patient by the breathing apparatus, and
establish leakage or abnormal resistance in the ventilation system based on the response in the bioelectric signal.

The change in the respiratory drive of the patient following a change in ventilatory assist can be seen as a measure of the "effectiveness" of the mechanical ventilation provided by the breathing apparatus, or the contribution of the mechanical ventilation in relation to the patient's own breathing, as further discussed in, e.g., U.S. Pat. No. 8,720,441 by Sinderby, and the co-pending international application PCT/SE2017/050096 by Halfback. The effectiveness of the mechanical ventilation mainly depends on the level of ventilatory assist, the patient interface (leakage/resistance) and the patient-ventilator synchrony, i.e., the synchrony between the patient's own breathing efforts and the delivery of breaths by the breathing apparatus.

In most circumstances, no change, or only a small change, in respiratory drive of the patient following a sufficiently large change in ventilatory assist is indicative of leakage or abnormal resistance in the ventilation system. Therefore, leakage or abnormal resistance in the ventilation system can be established by the control computer when the response in the bioelectric signal is small, e.g., when the change in magnitude and/or frequency of the bioelectric signal is below a certain threshold value, following a change in ventilatory assist that is sufficiently big, e.g., a change in ventilatory assist of at least 10%, preferably at least 20%, and even more preferably at least 30%. Hereinafter, no change, or only a small change, in respiratory drive of the patient following a substantial change (i.e., 10% or more from a previous level) in ventilatory assist will be referred to as a "small response" in respiratory drive.

In order to verify that a small response in respiratory drive is due to leakage or abnormal resistance in the ventilation system, it is preferably investigated whether the small response in respiratory drive is due to ineffectiveness of the mechanical ventilation or to a negligible contribution of the mechanical ventilation in relation to the patient's own breathing. Furthermore, if it is due to ineffectiveness of the mechanical ventilation, it may be desirable to further investigate whether the ineffectiveness of the mechanical ventilation depends on leakage or abnormal resistance, or some other phenomenon such as a deterioration of the patient's own lung function.

That the response in respiratory drive following a substantial change in ventilatory assist is small may be due to following phenomenon:
A) leakage or abnormal resistance in the ventilation system,
B) a maximum level of ventilatory assist has been exceeded, i.e., both the first and the second level of ventilatory assist are above a maximum level of ventilatory assist that is utilizable to the patient,
C) the contribution of the mechanical ventilation in relation to the patient's own breathing effort is negligible, i.e., both the first and the second level of ventilatory assist are below a minimum level of ventilatory assist that is utilizable to the patient, or
D) the breaths delivered by the breathing apparatus are delivered in asynchrony with the patient's own breathing efforts.

To exclude or render unlikely the possibility that the small response in respiratory drive of the patient depends on any of the reasons B-D, the method may comprise the steps of:
changing, a first time, the level of ventilatory assist from the first level of ventilatory assist to the second level of ventilatory assist,
determining a first response in the bioelectric signal to the first change in the level of ventilatory assist,
returning to the first level of ventilatory assist;
changing, a second time, the level of ventilatory assist from the first level of ventilatory assist to the second level of ventilatory assist,
determining a second response in the bioelectric signal to the second change in the level of ventilatory assist, and
establishing leakage or abnormal resistance in the ventilation system based on a comparison between the first and the second response.

The rationale behind this is to monitor for a change in the respiratory drive of the patient that occurs too suddenly to be explained by a change in the physiological status of the patient, e.g. by a change in the patient's ability to breath spontaneously. If such a sudden change in respiratory drive can be detected, it is likely to be caused by a leakage or abnormal resistance in the ventilation system.

To minimize the likelihood that the change in respiratory drive depends on a change in the physiological status of the patient, the time period between the first and the second change in ventilatory assist should not be too long. At the same time, it should not be too short as this would not allow the patient to return to a state of baseline ventilation prior to applying the second change in ventilatory assist, which in turn could introduce a difference between the responses that may be mistaken for being caused by a leakage or abnormal resistance. The time period between the first and the second change in ventilatory assist may, for example, be in the range of 1 to 5 minutes, and preferably in the range of 1-3 minutes.

If the first and the second response differ from each other, or if at least one of the first level and the second level of ventilatory assist is low enough, reason (B) above can be excluded. Also, as long as the breathing apparatus appears to function as intended and no settings or measurements point to the contrary, reason (D) above may be excluded. The latter (asynchrony) may also be excluded through an assessment of patient-ventilator synchrony. Reason (C) above may be more difficult to differentiate from reason (A) above but may, as mentioned above, be excluded based on a comparison between the first and the second response, for example in terms of magnitude and/or frequency of the bioelectric signal. For reasons further discussed in the detailed description following hereinafter, the difference between the first response and the second response is likely to be bigger if the small response is due to reason (A) than if it is due to reason (C).

Consequently, the method may further comprise a step of determining a difference between the first and the second response, and establishing leakage or abnormal resistance in the ventilation system when the difference exceeds a set threshold value.

The method may further comprise a step of determining when breaths are delivered by the breathing apparatus in synchrony with the patient's effort to breathe, i.e., a step of assessing patient-ventilator synchrony, and establishing leakage or abnormal resistance in the ventilation system only when synchrony can be verified. This step may be performed automatically, e.g., based on sensor measurements obtained in the ventilation system. For example, flow and/or pressure measurements obtained in the ventilation system may be compared with the measured bioelectric signal to automatically determine when breaths are delivered in synchrony with the patient's own breathing efforts.

Above, two different embodiments for detection of leakage and abnormal resistance based on changes in a monitored bioelectric signal have been proposed. The first embodiment, wherein leakage or abnormal resistance is established based on a change in the bioelectric signal during ventilation of the patient at a substantially constant level of ventilatory assist, allows for quick leakage/resistance detection and can be carried out without deviating from a desired baseline ventilation of the patient. The second embodiment, wherein leakage or abnormal resistance is established based on at least one response in the bioelectric signal to a change in the level of ventilatory assist provided to the patient, is not as quick as the first embodiment and requires the ongoing respiratory treatment of the patient to be altered. On the other hand, the second embodiment offers increased certainty in the leakage/resistance detection since it allows other phenomenon that otherwise may be mistaken for leakage or abnormal resistance in the ventilation system to be excluded.

The bioelectric signal may be any type of measurable bioelectric signal indicative of the breathing efforts of the patient. Non-exclusive examples of usable bioelectric signals are EMG (electromyogram) signals representing the electrical activity of the diaphragm or muscles in the upper airways (e.g. the laryngopharyngeal region), and EEG (electroencephalography) signals representing the electrical activity of respiratory centres of the brain.

The bioelectric sensor for detecting the bioelectric signal may be any type of bioelectric sensor capable of measuring a bioelectric signal indicative of the breathing efforts of the patient. In an exemplary embodiment, the bioelectric sensor comprises an oesophageal catheter carrying a number of electrodes for capturing EMG signals from the diaphragm and/or upper airways of the patient. An oesophageal catheter configured for detection of diaphragm EMG, i.e., the electrical activity of the diaphragm (EAdi), is often referred to as an Edi catheter in the field of NAVA ventilation, and the measured bioelectric signal representing the diaphragm EMG may be referred to as the Edi signal.

The method may be carried out during ventilation of the patient in a NAVA mode, in which the mechanical ventilation of the patient is controlled based on the Edi signal. For example, the mechanical ventilation may be controlled such that breaths are delivered to the patient by the breathing apparatus in synchrony with and/or in proportion to the Edi signal, and preferably both in synchrony with and in proportion to the Edi signal.

When the breathing apparatus is operated in NAVA mode, switching between the first and second levels of ventilatory assist may be performed by changing the NAVA level (NAVAg) determining the proportion of ventilatory assist in relation to the electrical activity of the diaphragm.

As mentioned above, the change in the level of ventilatory assist between the first level of ventilatory assist and the second level of ventilatory assist should be at least 10%, preferably at least 20%, and even more preferably at least 30%. Preferably, one of the first and second levels of ventilatory assist is a level of low or moderate ventilatory assist. In one exemplary embodiment, one of the first and the second levels of ventilatory assist is a level of zero ventilatory assist or a level of nearly zero ventilatory assist. In NAVA ventilation, a level of zero ventilatory assist corresponds to a continuous positive airway pressure (CPAP) or pressure support (PS) of 2 cmH2O above a set positive end-expiratory pressure (PEEP).

The method may be an intermittent method that is carried out with regular or irregular intervals. It may be initiated automatically or manually, and it may be carried out either completely automatically or partially automatically by the breathing apparatus.

Typically, the first level of ventilatory assist corresponds to a set desired level of ventilatory assist at which the patient is ventilated when not carrying out the method, i.e., a baseline level of ventilatory assist. Once the method is carried out, at least one breath is delivered to the patient at the second level of ventilatory assist, which may be higher or lower than the first level of ventilatory assist. In some embodiments, the second level of ventilatory assist is lower than the first level of ventilatory assist and may, for example, be delivered at a level of zero ventilatory assist. The at least one breath at the second level of ventilatory assist may hereinafter be referred to as a test breath.

In some embodiments, a plurality of consecutive test breaths may be delivered to the patient at the second level of ventilatory assist before switching back to the baseline level of ventilatory assist. In this scenario, the response in the bioelectric signal may be determined based on a mean or average value of the bioelectric signal during the plurality of the consecutive test breaths, e.g., as the root-mean-square (rms) value of the bioelectric signal during the plurality of consecutive test breaths. Since both the magnitude and the frequency of the bioelectric signal is expected to increase in response to the reduction in ventilatory assist it may be advantageous to take both the magnitude and frequency of the bioelectric signal into account in the determination of the response to the change in ventilatory assist.

The method may further comprise a step of communicating the establishment of leakage or abnormal resistance to an operator of the ventilation system. For example, the detection system may be configured to generate a visible, audible and/or tactile alarm signal upon establishment of leakage or abnormal resistance in the ventilation system.

Preferably but not necessarily, the detection system is integrated in the breathing apparatus of the ventilation system. In case the breathing apparatus is a NAVA-enabled ventilator, the bioelectric signal may be used by the control computer both for controlling the ventilator to provide mechanical ventilation of the patient in accordance with the well-known principles of NAVA, and for detection of leakage or abnormal resistance in the ventilation system according to the principles described herein.

Typically, the method is a computer-implemented method that is carried out automatically by the control computer upon execution of a computer program that is stored in a non-volatile memory of the detection system. In an embodiment, the computer program is embedded in the electronics of the control computer of a breathing apparatus.

Consequently, according to another aspect of the invention, there is provided a computer program for detection of leakage or abnormal resistance in a ventilation system comprising a breathing apparatus providing mechanical ventilation to a patient. The computer program comprises computer-readable code segments which, when executed by a control computer coupled to a bioelectric sensor arrangement for detecting a bioelectric signal indicative of the patient's effort to breathe, cause the control computer to:
 monitor a bioelectric signal indicative of the patient's effort to breathe;
 determine a change in the bioelectric signal, and
 establish leakage or abnormal resistance in the ventilation system based on the change in the bioelectric signal.

The computer program may further comprise code segments for causing the control computer to carry out any of the above described method steps. In particular, the computer program may be configured to cause the control computer to carry out the method in accordance with any of the first or second embodiment described above.

Consequently, in some embodiments, the computer program may cause the control computer to:
 control the breathing apparatus to ventilate the patient at a substantially constant level of ventilatory assist, and
 establish leakage or abnormal resistance in the ventilation system based on a change in the bioelectric signal occurring at the substantially constant level of ventilatory assist.

In other embodiments, the computer program may cause the control computer to:
 control the breathing apparatus to change a level of ventilatory assist provided to the patient from a first level of ventilatory assist to a second and different level of ventilatory assist;
 determine a response in the bioelectric signal to the change in level of ventilatory assist, and
 establish leakage or abnormal resistance in the ventilation system based on the response in the bioelectric signal.

The computer program may, for example, be stored in a non-volatile memory of the control computer. In another embodiment, the computer program is embedded in the electronics of the control computer of a breathing apparatus.

More advantageous aspects of the method, system and computer program according to the present disclosure will be described in the detailed description following hereinafter.

BRIEF DESCRIPTION OF DRAWINGS

A more complete appreciation of the invention disclosed herein will be obtained as the same becomes better understood by reference to the following detailed description when considered in conjunction with the accompanying drawings briefly described below, in which drawings the same reference numerals are used to represent corresponding functional elements.

DETAILED DESCRIPTION

It is generally assumed that the respiratory drive of a patient is primarily based on the CO2 content in the patient's blood, which in turn depends on the alveolar ventilation of the patient. Relying on this assumption, the present disclosure suggests using a bioelectric signal, indicative of a patient's respiratory drive, to detect leakage or abnormal resistance in a ventilation system. A detection system for detection of leakage or abnormal resistance in a ventilation system based on such a bioelectric signal will now be described with reference to an exemplary and non-limiting embodiment.

Figure 1:
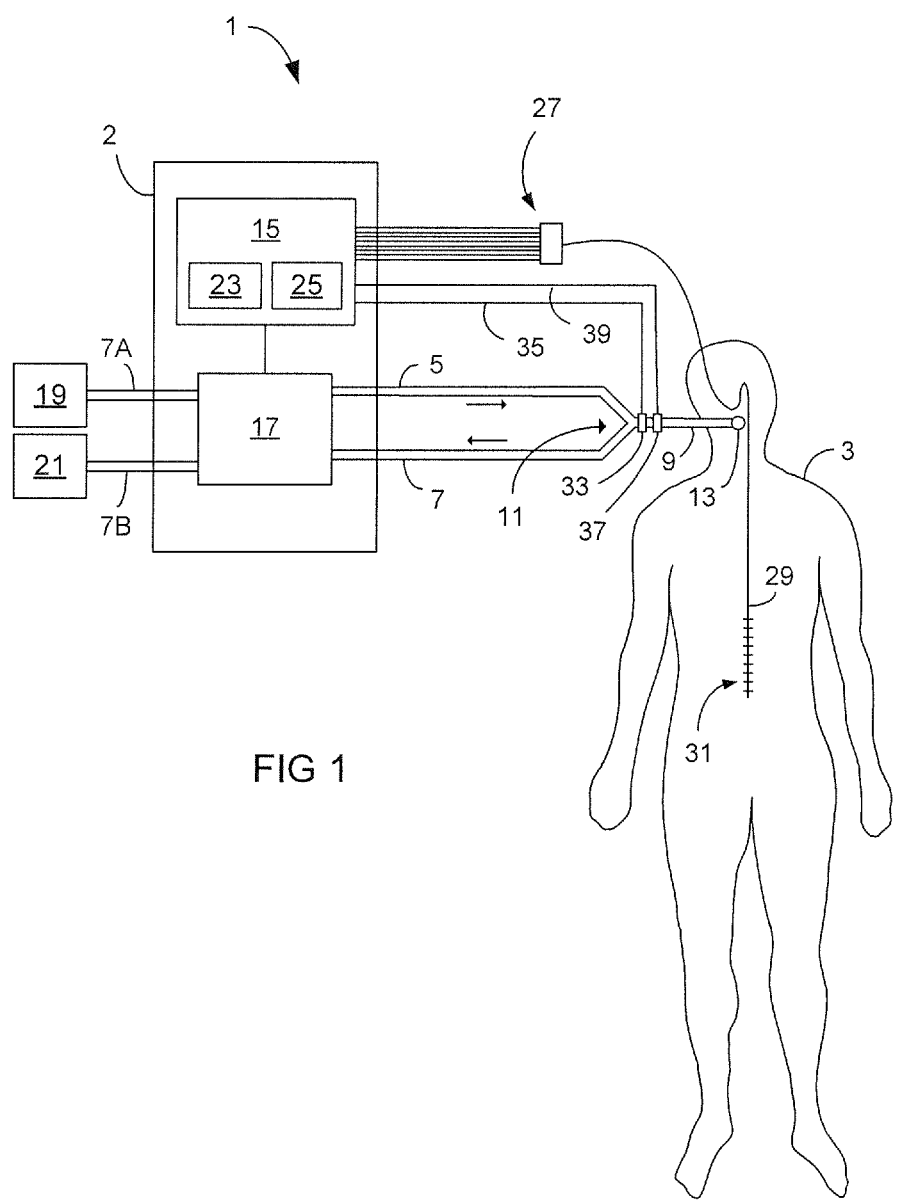
FIG. 1 illustrates a ventilation system comprising a detection system for detection of leakage or abnormal resistance in the ventilation system, according to an exemplary embodiment of the present disclosure.

FIG. 1 illustrates a ventilation system 1 comprising a breathing apparatus 2, such as a ventilator or an anaesthesia machine, for mechanical ventilation of a patient 3. The breathing apparatus 1 is connected to the patient 3 via an inspiratory line 5 for supplying breathing gas to the patient 3, and an expiratory line 7 for conveying expiration gas away from the patient 3. The inspiratory line 5 and the expiratory line 7 are connected to a common line 9, via a so called Y-piece 11, which common line is connected to the patient 3 via a patient connector 13, such as a facemask or an endotracheal tube.

The breathing apparatus 2 further comprises a control unit or control computer 15 for controlling the ventilation of the patient 3 based on pre-set parameters and/or measurements obtained by various sensors of the breathing apparatus. The control computer 15 controls the ventilation of the patient 3 by controlling a pneumatic unit 17 of the breathing apparatus 2, which pneumatic unit 17 is connected on one hand to one or more gas sources 19, 21 and on the other hand to the inspiratory line 5 for regulating a flow and/or pressure of breathing gas delivered to the patient 3. To this end, the pneumatic unit 17 may comprise various gas mixing and regulating means well known in the art of ventilation, such as gas mixing chambers, controllable gas mixing valves, turbines, controllable inspiration and/or expiration valves, etc.

The control computer 15 comprises a processor or processing unit 23, such as a microprocessor, and a non-volatile memory hardware device 25 storing one or more computer programs for controlling the operation of the breathing apparatus 1 and establishing leakage or abnormal resistance in the ventilation system 1 in accordance with the principles described herein. Unless stated otherwise, actions and method steps described hereinafter are performed by, or caused by, the control computer 15 of the breathing apparatus 2 upon execution by the processing unit 23 of different code segments of a computer program stored in the memory 25.

The breathing apparatus 2 further comprises a bioelectric sensor or bioelectric sensor arrangement 27 coupled to the control computer 15 of the breathing apparatus 1. The bioelectric sensor arrangement 27 is configured to detect bioelectric signals indicative of the patient's effort to breathe and to provide the bioelectric signals to the control computer 15 for use in the detection of leakage or abnormal resistance in the ventilation system 1, as will be described below.

In the exemplary embodiment illustrated in FIG. 1, the bioelectric sensor arrangement 27 is an EMG detector for recording the diaphragm EMG of the patient 3. To this end, the sensor arrangement 27 comprises an oesophageal catheter 29 carrying an array of electrodes 31 for capturing EMG signals from the diaphragm of the patient 3. The electrodes 31 produce a number of subsignals that are processed by the control computer 15 to calculate a signal, the Edi signal, representing the electrical activity of the diaphragm (EAdi) and, thus, indicative of the patient's effort to breathe. Since the EMG signals captured by the sensor are used to calculate an Edi signal, the oesophageal catheter 29 is often referred to as an Edi catheter within the field of ventilation.

Although exemplified in form of an Edi catheter, it should be understood that the bioelectric sensor arrangement 27 could be any known bioelectric sensor arrangement for detection of bioelectric signals indicative of the patient's effort to breath and, thus, indicative of what is herein referred to as the respiratory drive of the patient 3. For example, the bioelectric sensor arrangement 27 could comprise a number of surface electrodes placed on the ribcage, the abdomen or in the vicinity of the phrenic nerve of the patient 3 to sense and filter out diaphragmatic EMG signals to be used in the detection of leakage or abnormal resistance in the ventilation system 1. According to another example, the bioelectric sensor arrangement could be devised to detect laryngopharyngeal EMG signals of the patient 3, indicative of the electric activity of respiratory muscles in the laryngopharyngeal region of the patient 3, e.g., the thyroarytenoid and cricothyroid muscles, and to use the laryngopharyngeal EMG signals in the detection of leakage or abnormal resistance in the ventilation system 1. Examples of suitable bioelectric sensor arrangements for detection of laryngopharyngeal EMG signals that may be used in the detection of leakage or abnormal resistance in the ventilation system are disclosed in international patent application WO2016/153406 by the same applicant.

The breathing apparatus 2 may be any type of breathing apparatus and operated in any type of support ventilation mode, such as a mode of pressure support ventilation (PSV) or volume support ventilation (VSV). If the breathing apparatus 2 is operated in PSV, VSV or any other ventilation mode in which the ventilation of the patient 3 is not controlled based on the bioelectric signal captured by the bioelectric sensor arrangement 27, the bioelectric signal may still be captured and used for the sole purpose of detecting leakage or abnormal resistance using the principles described herein.

Preferably, however, the breathing apparatus 2 is configured to be operated in a bioelectrically controlled mode of ventilation in which the control computer 15 controls the pneumatic unit 17 and hence the ventilation of the patient 3 based on the bioelectric signals detected by the bioelectric sensor arrangement 27.

That the control computer 15 controls the ventilation of the patient 3 based on the bioelectric signal captured by the bioelectric sensor arrangement 27 means that the bioelectric signal is used by the control computer 15 at least for the triggering of breaths that are to be delivered to the patient 3, i.e., for determining the onset time of inspiration phases. The bioelectric signal may also be used by the control computer 15 to control other breath-related parameters, such as the airway pressure applied during the breath, the time for cycle-off of the breath, etc. Preferably, the bioelectric signal is used by the control computer 15 to control both the timing and the size of the breaths delivered to the patient 3.

In the illustrated embodiment, the breathing apparatus 2 is configured to be operated in NAVA mode in which the Edi signal captured by the bioelectric sensor arrangement 27 is used to deliver breathing gas to the patient 3 in synchrony with and in proportion to the patient's own effort to breathe, as described in greater detail in, for example, WO1998/48877, WO1999/62580, WO2006/131149, and WO2008/131798.

The breathing apparatus 1 may further comprise a flow sensor 33 for measuring patient flow. The flow sensor 33 is configured to measure at least an inspiratory flow of breathing gas delivered the patient 3 during inspiration phases. Preferably, the flow sensor 33 is configured to measure also an expiratory flow of expiration gas exhaled by the patient during expiration phases. In the exemplary embodiment illustrated in FIG. 1, the flow sensor 33 is located in or close to the Y-piece 11 and configured to measure both inspiratory and expiratory flows. The measurement signals obtained by the flow sensor 33 are transmitted to the control computer 15 via a signalling line 35, whereby the measurement signals may be used by the control computer 15 for patient monitoring and/or to control the ventilation of the patient 3. In other embodiments, a first flow sensor for measuring the inspiratory flow of breathing gas delivered to the patient 3 may be arranged within an inspiratory module of the breathing apparatus 2, whereas a second flow sensor for measuring an expiratory flow of expiration gas exhaled by the patient 3 may be arranged within an expiratory module of the breathing apparatus 2. The patient flow measurements may further be used by the control computer 15 to calculate inspiratory and/or expiratory volumes of gas inhaled and/or exhaled by the patient 3.

Furthermore, the control computer 15 may be configured to obtain measurements of a pressure applied to the patient 3 during inspiration and/or expiration, for example from a pressure sensor 37 of the breathing apparatus 1. In the exemplary embodiment illustrated in FIG. 1, the pressure sensor 37 is located in or close to the Y-piece 11 and configured to measure a pressure substantially corresponding to the airway pressure of the patient 3. The measurement signals obtained by the pressure sensor 37 are transmitted to the control computer 15 via a signalling line 39, whereby the measurement signals may be used by the control computer 15 for patient monitoring and/or for controlling the ventilation of the patient 3. In other embodiments, one or more pressure sensors for measuring one or more pressures from which the airway pressure of the patient 3 can be derived may be arranged within an inspiratory module and/or an expiratory module of the breathing apparatus 1.

The breathing apparatus 2 and, more specifically, the control computer 15 of the breathing apparatus 2, is configured to detect leakage or abnormal resistance in the ventilation system 1 based on the bioelectric signals captured by the bioelectric sensor arrangement 27, meaning that it is configured to monitor and analyse the bioelectric signals to detect events that are indicative of leakage or abnormal resistance in the ventilation system 1.

The control computer 15 is configured to determine a change in the bioelectric signal and to establish leakage or abnormal resistance in the ventilation system 1 based on the change in the bioelectric signal.

According to a first embodiment, this may be achieved by monitoring the bioelectric signal during ventilation of the patient 3 at a substantially constant level of ventilatory assist. This means that the level of breathing support provided to the patient 3 by the breathing apparatus 2 is kept at a substantially constant level. The control computer 15 is configured to detect a change in the bioelectric signal and to determine whether a detected change in the bioelectric signal is indicative of a leakage or abnormal resistance in the ventilation system 1. This may, for example, be achieved by the control computer 15 by determining when a detected change in the bioelectric signal exceeds a set threshold value. In one exemplary embodiment, the control computer 15 may be configured to determine a reference value for the monitored bioelectric signal from a bioelectric signal registered at the same level of ventilatory assist at a previous point in time at which there was no leakage or abnormal resistance in the ventilation system, and to determine when the monitored bioelectric signal deviates from the reference value by a set amount, for example when the monitored bioelectric signal deviates from the reference value by 10%, 20% or 30%.

According to a second embodiment, leakage or abnormal resistance in the ventilation system 1 may be established by the control computer 15 based on at least one response in the bioelectric signal to a change in the level of ventilatory assist provided to the patient 3.

With simultaneous reference to the system in FIG. 1, the rationale behind the second embodiment will now be described with reference to FIG. 2.

Figure 2:
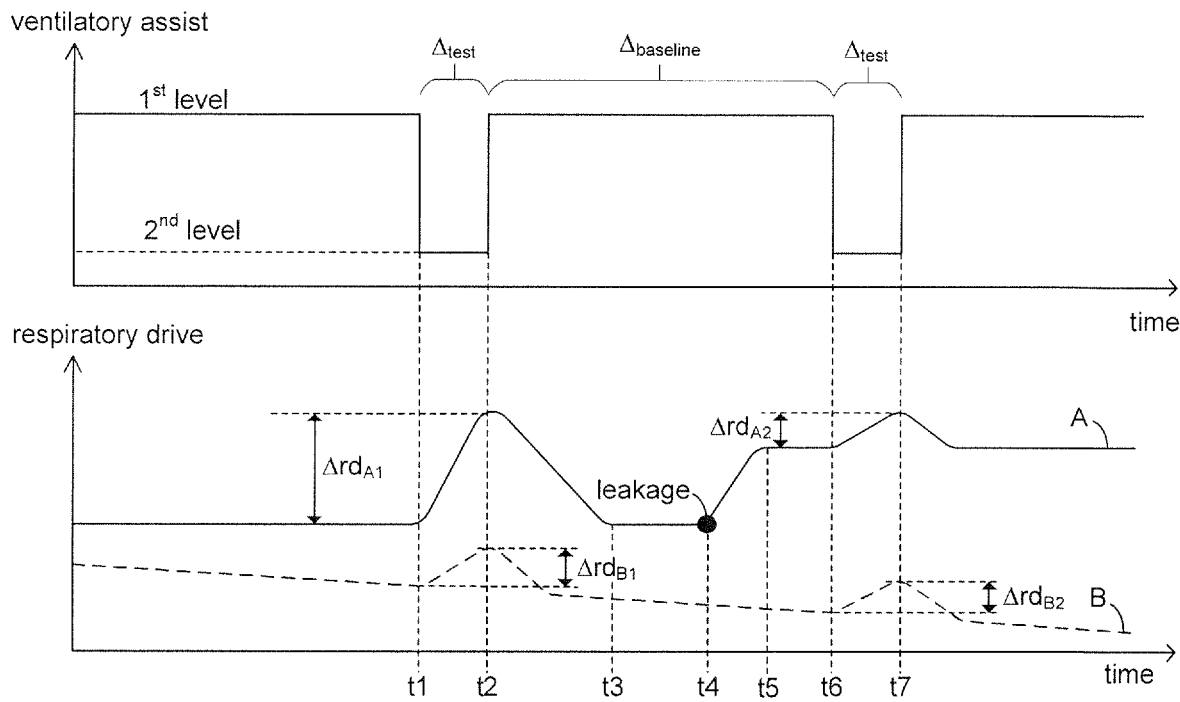
FIG. 2 illustrates an exemplary ventilation pattern that may be applied to the patient in order to detect leakage or abnormal resistance in the ventilation system, and variations in the respiratory drive of the patient, partly caused by the ventilation pattern.

FIG. 2 shows an upper diagram illustrating a ventilation pattern that may be applied to the patient 3 by the breathing apparatus 2, according to an exemplary embodiment of the present disclosure. During ventilation of the patient 3, the control computer 15 causes the level of ventilatory assist applied to the patient 3 by the breathing apparatus 2 to be changed from a first level of ventilatory assist to a second and substantially different level of ventilatory assist. The control computer 15 determines the response in the bioelectric signal to the change in ventilatory assist, and determines if the response indicates that leakage or abnormal resistance is present in the ventilation system 1.

In the illustrated scenario, the patient 3 is ventilated at a first level of ventilatory assist, corresponding to a baseline level of ventilatory assist that may be selected either manually or automatically based on the need for unloading of the patient's lungs. The type of ventilatory assist provided to the patient depends on the current mode of operation of the breathing apparatus 2 and may, for example, be defined by an inspiratory pressure that is applied to the patient during inspiration or a tidal volume that is delivered to the patient during inspiration. The curve in the upper diagram may hence, in some exemplary embodiments, represent the pressure applied to the patient 3 during inspiration. In the illustrated embodiment in which the breathing apparatus 2 is operated in NAVA mode, the ventilatory assist may be defined by the NAVA level (NAVAg) determining the proportion of ventilatory assist in relation to the electrical activity of the diaphragm. Consequently, the curve in the upper diagram of FIG. 2 may represent the NAVA level of the ongoing NAVA ventilation.

At a certain point in time, t1, the level of ventilatory assist is changed from the baseline level to the second level of ventilatory assist, hereinafter referred to as the test level. The change may be either an increase or a decrease in ventilatory assist. The change should be big enough to ensure a distinct response in the bioelectric signal, and the level of ventilatory assist should preferably be increased or decreased by at least 10%, more preferably by at least 20%, and most preferably by at least 30%. In the illustrated embodiment, the breathing apparatus 2 is operated in NAVA mode and the test level is a level of zero ventilatory assist (NAVAg=0), which corresponds to a continuous positive airway pressure (CPAP) or pressure support (PS) of 2 cmH2O above a set positive end-expiratory pressure (PEEP).

If the ventilatory assist provided by the breathing apparatus 2 really helps in unloading the patient's lungs, which it generally does as long as the patient 3 is incapable of breathing on his own, the abrupt decrease in ventilatory assist at t1 will increase the patient's hunger for breathing gas and, thus, increase the respiratory drive of the patient 3, meaning that more and/or stronger signals will be sent to the respiratory muscles of the patient from the respiratory centre of the patient's brain, in an attempt to increase breathing. This, in turn, causes an increase in the electrical activity of the respiratory muscles, including the EAdi of the diaphragm, which is reflected by the bioelectric signal captured by the bioelectric sensor arrangement 27. Consequently, the respiratory drive of the patient 3, as reflected by the bioelectric signal, is expected to increase in response to the decrease in ventilatory assist at t1.

As indicated by the continuous line A in the lower diagram of FIG. 2, representing the respiratory drive of a typical patient subjected to the exemplary ventilation pattern in the upper diagram, the respiratory drive A of the patient 3 changes by a magnitude $\Delta rd_{A1}$ in response to the change in ventilatory assist at t1. At a point in time t2, the level of ventilatory assist is switched back to the baseline level, whereupon the respiratory drive of the patient 3 typically returns gradually to a level corresponding to the respiratory drive of the patient prior to the change in ventilatory assist, which level may be regarded as a baseline level of respiratory drive corresponding to the baseline level of ventilatory assist.

The duration of the test period, $\Delta_{test}$, i.e. the period during which the ventilatory assist is maintained at the test level (e.g., the time between t1 and t2), may be one or several breaths. In some embodiments, the duration of the test period may be long enough for the respiratory drive of the patient 3 to reach a new substantially steady state, meaning that the respiratory drive of the patient 3 is allowed to reach a substantially constant level that is different than the baseline level of respiratory drive. In other embodiments, the duration of the test period may be too short for the respiratory drive of the patient 3 to reach a new level of steady state, whereby only the initial response in the bioelectric signal to the change in ventilatory assist is studied and used in the detection of leakage or abnormal resistance in the ventilation system 1. In embodiments where the test period comprises a plurality (i.e., two or more) of breaths delivered at the test level of ventilatory assist, the response in the bioelectric signal may be determined by the control computer 15 based on a mean or average value of the bioelectric signal during the plurality of the consecutive test breaths, e.g., as the root-mean-square (rms) value of the bioelectric signal during the plurality of consecutive test breaths.

As long as the physiological state of the patient 3 and the operation of the breathing apparatus 2 remain constant, a similar change in ventilatory assist can be assumed to generate a similar response in the respiratory drive of the patient and, thus, in the bioelectric signal. If, however, the change or response $\Delta rd$ in respiratory drive is smaller than expected following a substantial change in ventilatory assist, such as a change from a baseline level of ventilatory assist to a low or zero level of ventilatory assist, the physiological state of the patient or the operation of the breathing apparatus 2 can be assumed to have changed.

In certain circumstances, a small response in the bioelectric signal following a substantial change in ventilatory assist can only be explained by a leakage or abnormal resistance in the ventilation system 1. In this situation, the control computer 15 may establish the occurrence of a leakage or abnormal resistance based on the response in the bioelectric signal, and take appropriate actions, for example generating an alarm signal to alert an operator of the conditions of the ventilation system 1. To determine when the response in the bioelectric signal is small enough to indicate leakage or abnormal resistance, the control computer 15 may be configured to compare the response with a set threshold value. The threshold value may be set by the operator of the ventilation system 1 or calculated by the control computer 15 based on patient parameters and/or ventilator parameters input to the breathing apparatus 2 by the operator, and/or sensor data obtained by various sensors of the ventilation system 1. For example, the threshold value may be calculated by the control computer 15 based on the first and second levels of ventilatory assist and, optionally, based on patient-related parameters indicative of an expected response in respiratory drive to a change in ventilatory assist between the first and second levels of ventilatory assist. The threshold value may also be calculated by the control computer 15 based on historical data on the bioelectric signal, for example, based on one or more previous responses in the bioelectric signal following a change in ventilatory assist between the first and second levels of ventilatory assist.

In the scenario illustrated by curve A in FIG. 2, a leakage or abnormal resistance in the ventilation system 1 occurs at a point in time t4. Due to the leakage or abnormal resistance, the efficiency of the mechanical ventilation of the patient 3 is reduced and, as a consequence, the respiratory drive of the patient 3 increases. In this exemplary scenario, the respiratory drive of the patient increases until it reaches a new substantially steady state at a point in time t5. When, at a point in time t6, the ventilatory assist is once again changed from the baseline level to the test level, the response $\Delta rd_{A2}$ in the respiratory drive as reflected by the bioelectric signal is considerably smaller in magnitude than the response $\Delta rd_{A1}$ to the first change in ventilatory assist. Based on the response $\Delta rd_{A2}$, the control computer 15 can establish that a leakage or abnormal resistance has occurred in the ventilation system 1, e.g., from a comparison of the response $\Delta rd_{A2}$ with the above mentioned threshold value, revealing that the response is small enough to suspect leakage or abnormal resistance.

Preferably, the ventilation pattern applied to the patient 3 by the breathing apparatus 2 is a periodic ventilation pattern with alternating periods of ventilatory assist at the baseline level and ventilatory assist at the test level. The periods of ventilatory assist at the baseline level should preferably have a duration, $\Delta_{baseline}$, that is long enough in order for the respiratory drive of the patient 3 to return to the baseline level of respiratory drive (which occurs at t3 in FIG. 2) prior to a subsequent change in ventilatory assist from the baseline level to the test level. This is important as the uncertainty in the proposed method may increase unless the respiratory drive of the patient is substantially the same at the start of the different test periods. That the periods of ventilatory assist at the baseline level are long enough in relation to the test periods is also important to ensure that the patient 3 receives adequate overall ventilation. However, as will be further discussed below, should the period of ventilatory assist at the baseline level be too long, there is a risk that changes in the patient's capacity of spontaneous breathing are mistaken for leakage or abnormal resistance in the ventilation system 1. Therefore, the duration of the period of baseline ventilation is preferably in the range of 1-5 minutes, and more preferably in the range of 1-3 minutes.

As discussed above, a small response in respiratory drive following a substantial change in ventilatory assist may be due also to other phenomenon than leakage or abnormal resistance in the ventilation system. Any of, or any combination of, the following phenomenon may be the underlying cause of a small response in respiratory drive:

A) leakage or abnormal resistance in the ventilation system 1,
B) "Over-assist": a maximum level of ventilatory assist has been exceeded, meaning that both the first and the second level of ventilatory assist are above a maximum level of ventilatory assist that is utilizable to the patient 3,
C) "Under-assist": the contribution of the mechanical ventilation in relation to the patient's own breathing effort is negligible, meaning that both the first and the second level of ventilatory assist are below a minimum level of ventilatory assist that is utilizable to the patient 3, or
D) "Asynchrony": the breaths delivered by the breathing apparatus 2 are delivered in asynchrony with the patient's own breathing efforts.

With reference still made to FIGS. 1 and 2, the control computer 15 may be configured to exclude or render unlikely the possibility that a small response in respiratory drive following a change in ventilatory assist depends on any of the reasons B-D by comparing the small response with at least one previous response in respiratory drive to the same change in ventilatory assist. "Same change" here means that the changes in ventilatory assist should be identical in terms of both the start level (i.e., the level of ventilatory assist prior to the change) and end level (i.e., the level of ventilatory assist after the change). With reference again made to curve A in FIG. 2, this means that the control computer 15 may compare the small response $\Delta rd_{A2}$ in respiratory drive, following the change in ventilatory assist at t6, with the previous response $\Delta rd_{A1}$, following the same change in ventilatory assist at t1. Based on the result of the comparison, the control computer 15 may exclude that the small response $\Delta rd_{A2}$ is due to under-assist (reason C), and so that the small response is likely to be caused by a leakage or abnormal resistance in the ventilation system 1.

If a first response in the respiratory drive following a substantial change in ventilatory assist is small due to under-assist, responses in the respiratory drive following subsequent and identical changes in ventilatory assist are unlikely to differ substantially from the first response. Small differences between the responses may occur due to the fact that the capability of spontaneous breathing of the patient 3 may change over time. However, even if so, the difference between responses in the respiratory drive to identical changes in ventilatory assist will in general be very small, at least as long as the time period between each test period is not too long.

The curve B in FIG. 2 illustrates an exemplary scenario of under-assist in which the capability of spontaneous breathing of the patient 3 improves over time. In this scenario, the response $\Delta rd_{B1}$ in the respiratory drive of the patient 3 to the first change in ventilatory assist at t1, as reflected by the captured bioelectric signal, is seen to be small due to the fact that the baseline level of ventilatory assist provided by the breathing apparatus 2 makes up for only a small part of the patient's breathing, meaning that the baseline level of ventilatory assist is low in relation to the spontaneous breathing capacity of the patient 3. When the second change in ventilatory assist is applied, at the point in time t6, the spontaneous breathing capacity of the patient 3 has further improved, resulting in an even smaller response $\Delta rd_{B2}$ in respiratory drive. However, the improvement of the patient's capability of spontaneous breathing is a slow process and, therefore, the difference between the first response $\Delta rd_{B1}$ and the second response $\Delta rd_{B2}$ in respiratory drive of the patient 3 is very small compared to the difference between the first response $\Delta rd_{A1}$ and the second response $\Delta rd_{A2}$ in respiratory drive of the patient 3 in the scenario illustrated by curve A, in which the small response $\Delta rd_{A2}$ in respiratory drive is caused by leakage or abnormal resistance in the ventilation system 1.

Consequently, to distinguish leakage or abnormal resistance from under-assist, the control computer 15 may be configured to compare a first response in the captured bioelectric signal, caused by a first change in ventilatory assist, with a second response in the captured bioelectric signal, caused by a second change in ventilatory assist, identical to the first change in ventilatory assist, and to establish leakage or abnormal resistance in the ventilation system 1 when there is a substantial change between the first and the second response.

To exclude the possibility that a small response in respiratory drive following a substantial change in ventilatory assist is due to over-assist (reason B), at least one of the first and second levels of ventilatory assist should be low enough to guarantee that it does not exceed a maximum level of ventilatory assist that is utilizable to the patient. That the maximum level of ventilatory assist is a maximum level of ventilatory assist that is "utilizable to the patient" means that increasing the level of ventilatory assist above the maximum level of ventilatory assist does not further unload the lungs of the patient. Thus, at least one of the first and second levels of ventilatory assist, and preferably the second level at which ventilatory assist is provided during the relatively short test periods, should correspond to a low or moderate level of ventilatory assist, such as a zero or near zero level of ventilatory assist.

To exclude the possibility that a small response in respiratory drive following a substantial change in ventilatory assist is due to asynchrony (reason D), the control computer 15 may be configured to perform any method known in the art for assessing patient-ventilator synchrony. To this end, the control computer 15 may use flow and/or pressure measurements obtained by the flow sensor 33 and/or the pressure sensor 37, and compare the timing of delivery of breaths by the breathing apparatus 2, as indicated by the flow and/or pressure measurements, with the timing of the patient's breathing efforts, as indicated by the bioelectric signal. For example, the control computer 15 may be configured to determine an index of patient-ventilator interaction in accordance with the principles described in "An automated and standardized neural index to quantify patient-ventilator interaction" by Sinderby et al., Critical Care 2013, 17:R239, and use the index to verify patient-ventilator synchrony. If the control computer 15 can verify patient-ventilator synchrony, i.e., that breaths are delivered by the breathing apparatus 2 in synchrony with the patient's own breathing efforts, asynchrony can be excluded as the underlying cause to only a small change in respiratory drive following a substantial change in ventilatory assist.

Consequently, according to some embodiments, the control computer 15 of the breathing apparatus 2 may be configured to establish leakage or abnormal resistance in the ventilation system 1 not only based on a response in the bioelectric signal to a change in ventilatory assist, but also based on a comparison between a first response and a second response in the bioelectric signal, caused by identical changes in ventilatory assist applied to the patient 3 at different points in time, and an assessment of patient-ventilator synchrony. In this case, given that at least one of the levels of ventilatory assist is low enough to exclude over-assist, leakage or abnormal resistance in the ventilation system can be established with a high degree of certainty.

FIGS. 3-6 illustrate embodiments of a method for detection of leakage or abnormal resistance in a ventilation system. The method is preferably a computer implemented method that is automatically performed by the breathing apparatus 2 upon execution by the control computer 15 of a computer program stored in the non-volatile memory 25, which computer program comprises instructions that cause the breathing apparatus 2 to perform the various method steps.

Figure 3:
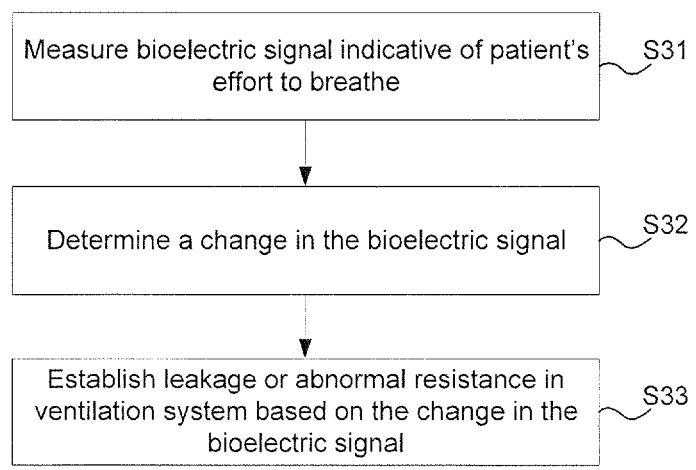
FIGS. 3-6 are flowcharts illustrating exemplary embodiments of a method for detection of leakage or abnormal resistance in the ventilation system.

With reference first made to FIG. 3 the method comprises a first step, S31, of measuring a bioelectric signal indicative of the patient's effort to breathe. In a second step, S32, a change in the measured bioelectric signal is determined, and, in a third step, S33, leakage or abnormal resistance in the ventilation system is established based on the change in the bioelectric signal. Step S31 is performed by the array of electrodes 31 of the bioelectric sensor arrangement 27. Steps S32 and S33 are performed by the processor 23 of the control computer 15.

Figure 4:
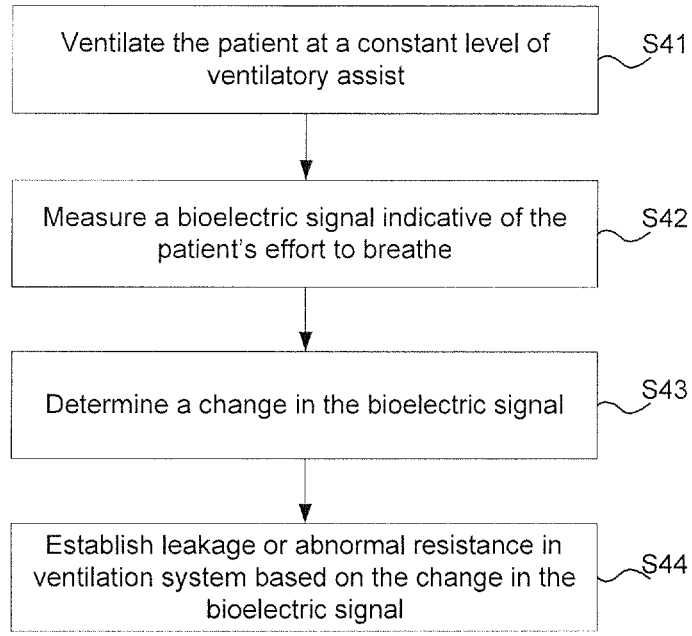

FIG. 4 illustrates how the method may be conducted according to a first embodiment where leakage or abnormal resistance is established based on a change in the bioelectric signal during ventilation of the patient at a substantially constant level of ventilatory assist.

In a first step, S41, the patient 3 is ventilated at a substantially constant level of ventilatory assist. Typically, this is achieved by the control computer 15 by controlling the breathing apparatus 2 to ventilate the patient 3 at a desired baseline level of ventilatory assist. In a second step, S42, a bioelectric signal indicative of the patient's effort to breathe is measured during ventilation of the patient at the substantially constant level of ventilatory assist. In a third step, S43, a change in the measured bioelectric signal is determined, and, in a fourth step, S44, leakage or abnormal resistance in the ventilation system is established based on the change in the bioelectric signal. Step S42 is performed by the array of electrodes 31 of the bioelectric sensor arrangement 27. Steps S43 and S44 are performed by the processor 23 of the control computer 15.

Figure 5:
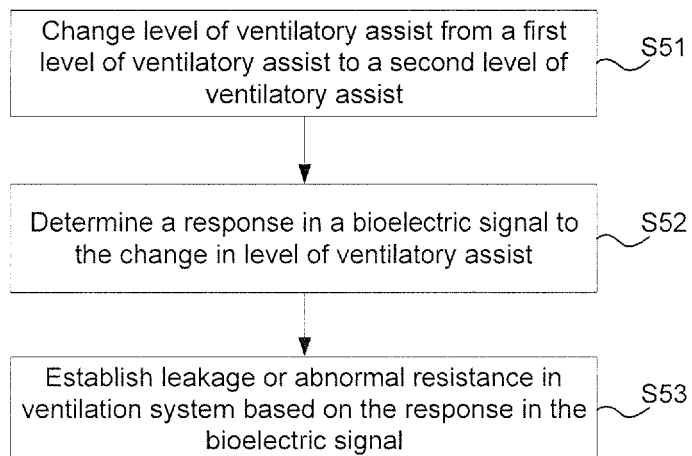
Figure 6:
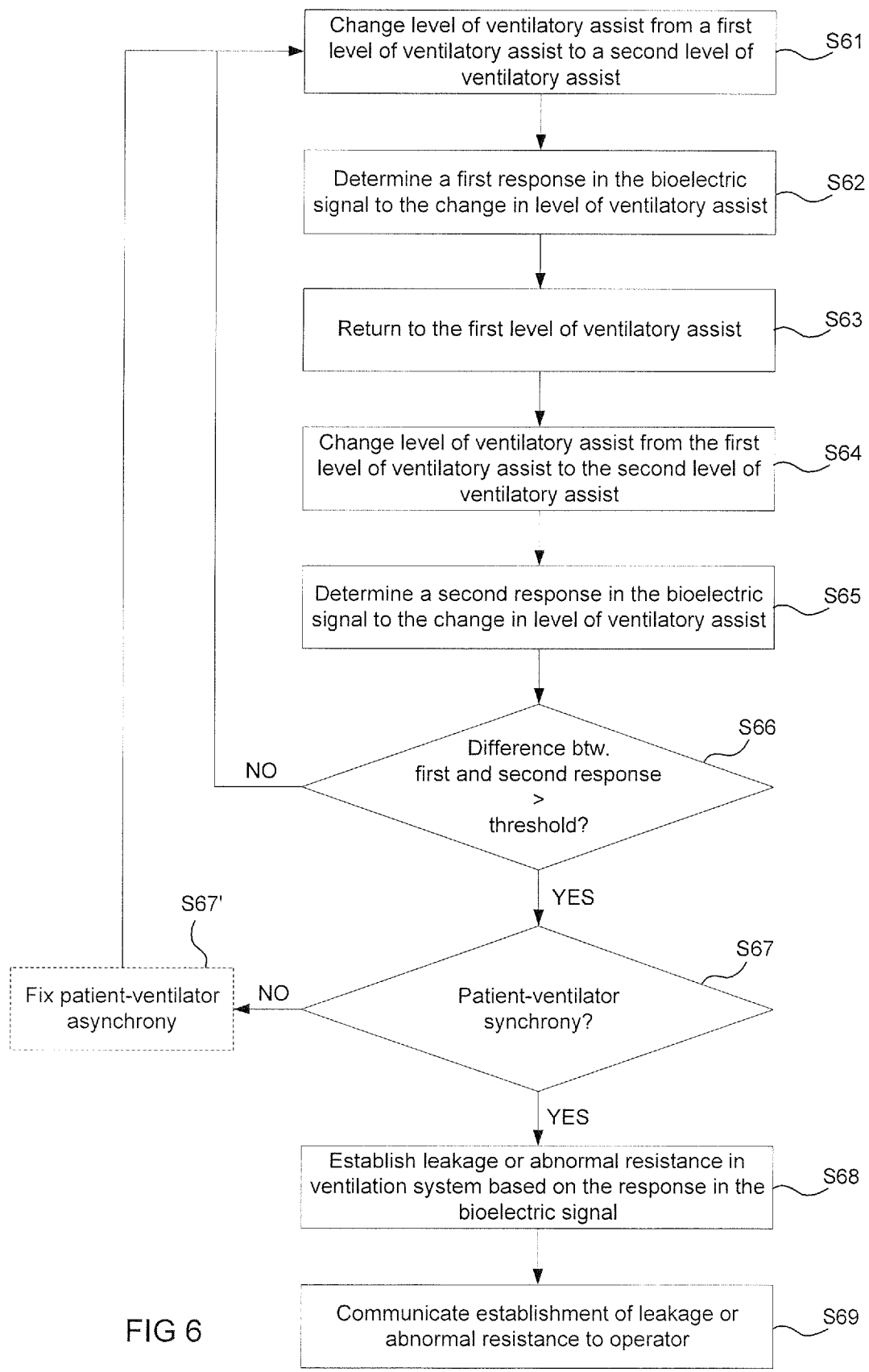

FIGS. 5 and 6 illustrate how the method may be conducted according to a second embodiment where leakage or abnormal resistance is established based on at least one response in the bioelectric signal to a change in the level of ventilatory assist provided to the patient.

With reference now made to FIG. 5, the method comprises a first step S51 of changing a level of ventilatory assist, provided to the patient 3 by the breathing apparatus 2, from a first level of ventilatory assist to a second level of ventilatory assist. Step S51 may be performed by the control computer 15. In a second step, S52, a change in a bioelectric signal, caused by the change in the level of ventilatory assist, is determined from a measured bioelectric signal indicative of the patient's efforts to breath. Thus, step S52 may involve the array of electrodes 31 of the sensor arrangement 27 and the processor 23 of the control computer 15. This change is herein referred to as the response in the bioelectric signal to the change in ventilatory assist. In a third and final step, S53, the response in the bioelectric signal is analysed to establish whether or not there is a leakage or abnormal resistance in the ventilation system 1. Typically, the analysis comprises comparing the response in the bioelectric signal with a threshold value, whereby leakage or abnormal resistance can be established if the response is smaller than the threshold value. Step S53 is performed by the processor 23 of the control computer 15.

With reference now made to FIG. 6, illustrating a refined embodiment of the method disclosed in FIG. 5, wherein the certainty in the establishment of leakage or abnormal resistance is increased by excluding other phenomenon which, besides leakage or abnormal resistance in the ventilation system, may cause the response in the bioelectric signal following a substantial change in ventilatory assist to be small.

In a first step, S61, the level of ventilatory assist is changed from a first level of ventilatory assist to a second level of ventilatory assist. Step S61 may be performed by the control computer 15, which controls the pneumatic unit 17 of the breathing apparatus 2. The second level of ventilatory assist is selected to be below a maximum level of ventilatory assist that is utilizable to the patient. This has the above described effect of preventing changes in the respiratory drive of the patient caused by over-assist to be mistaken for changes caused by leakage or abnormal resistance in the ventilation system. In a second step, S62, a first response in the bioelectric signal to the change in level of ventilatory assist in step S61 is determined. This step may involve the array of electrodes 31, which provide a bioelectric signal that is assessed by the processor 23 of the control computer 15. In a third step, S63, the level of ventilatory assist is returned to the first level of ventilatory assist. Step S63 is performed by the control computer 15 controlling the pneumatic unit 17. In a fourth step, S64, the level of ventilatory assist is once again changed from the (same) first level of ventilatory assist to the (same) second level of ventilatory assist. Step S64 is performed by the control computer 15 controlling the pneumatic unit 17. In a fifth step, S65, a second response in the bioelectric signal to the change in level of ventilatory assist in step S64 is determined. This step may involve the array of electrodes 31, which provide a bioelectric signal that is assessed by the processor 23 of the control computer 15. In a sixth step, S66, the first and the second response in the bioelectric signal are compared with each other. If there is not a substantial difference between the first and the second response, a leakage or abnormal resistance in the ventilation system 1 is unlikely to have occurred between the test periods (i.e., between determination of the first response in step S62 and the determination of the second response in step S65), and the method returns to step S61. If, however, there is a substantial difference between the first response and the second response, e.g., if the difference exceeds a certain threshold value, a leakage or abnormal resistance in the ventilation system 1 may have occurred between the test periods. Step S66 is performed by the processor 23 of the control computer 15. Besides establishing that a leakage or abnormal resistance may have occurred, the comparison of the first and second response has the above described effect of preventing changes in the respiratory drive of the patient caused by under-assist to be mistaken for changes caused by leakage or abnormal resistance in the ventilation system. In a seventh step, S67, it is assessed whether breaths are delivered by the breathing apparatus 2 in synchrony with the patient's own breathing efforts, i.e., whether patient-ventilator synchrony prevails. Processor 23 may be employed to make this synchrony determination. If it can be verified that patient-ventilator synchrony prevails, or at least that patient-ventilator asynchrony does not prevail, the method proceeds to step S68. Otherwise, the method returns to step S61, preferably via an optional step S67' in which the patient-ventilator asynchrony is eliminated or alleviated by any means available in the art. In step S68, it is established that there is leakage or abnormal resistance in the ventilation system 1 since the difference between the first and the second response in the bioelectric signal cannot be explained by any other phenomenon. Step S68 is performed by the processor 23 of the control computer 15. In a final step, S69, the establishment of leakage or abnormal resistance in the ventilation system 1 is communicated to an operator of the ventilation system 1, for example through generation of a visible, audible and/or tactile alarm signal, such as may be generated by a notification system. Upon noticing the alarm, the operator may perform an ocular inspection of the ventilation system 1, and in particular the patient connector 13 of the patient interface, in order to remove the cause of the leakage or abnormal resistance in the ventilation system 1.

The invention claimed is:

1. A method for detection of leakage or abnormal resistance in a ventilation system, the ventilation system including a breathing apparatus configured to provide a mechanical ventilation to a patient, comprising:
   measuring, using a bioelectric sensor, a bioelectric signal indicative of the patient's effort to breathe;
   determining, using a processor of the breathing apparatus, a change in the bioelectric signal; and
   determining, using the processor, leakage or abnormal resistance in the ventilation system based on the change in the bioelectric signal,
   wherein the bioelectric signal is at least one of an Edi signal or an EMG signal, indicative of electrical activity of the patient's respiratory muscles, or an EEG signal indicative of electrical activity of the patient's respiratory centres of a brain, and
   wherein the method is performed during ventilation of the patient in a ventilation mode in which the mechanical ventilation of the patient is controlled based on the bioelectric signal.

2. The method of claim 1, further comprising:
   changing, using a control computer of the breathing apparatus, a level of ventilatory assist provided to the patient from a first level of ventilatory assist to a second level of ventilatory assist, the first level being different from the second level;
   determining, using the processor, a response ($\Delta rd_{A2}$) in the bioelectric signal to the change in level of ventilatory assist; and
   determining, using the processor, whether there is a leakage or abnormal resistance in the ventilation system based on the response in the bioelectric signal.

3. The method of claim 2, further comprising:
   changing, a first time, the level of ventilatory assist from the first level of ventilatory assist to the second level of ventilatory assist;
   determining a first response ($\Delta rd_{A1}$) in the bioelectric signal to the first change in the level of ventilatory assist;
   changing, a second time, the level of ventilatory assist from the first level of ventilatory assist to the second level of ventilatory assist;
   determining a second response ($\Delta rd_{A2}$) in the bioelectric signal to the second change in the level of ventilatory assist, and determining leakage or abnormal resistance in the ventilation system based on a comparison between the first and second responses.

4. The method of claim 3, wherein the step of establishing leakage or abnormal resistance includes the following substeps of:
determining a difference between the first response ($\Delta rd_{A1}$) and the second response ($\Delta rd_{A2}$), and
determining leakage or abnormal resistance in the ventilation system when the difference between the first response and the second response exceeds a set threshold value.

5. The method of claim 1, wherein the bioelectric signal is measured during ventilation of the patient at a substantially constant level of ventilatory assist, and wherein leakage or abnormal resistance in the ventilation system is determined when the change in the bioelectric signal indicates an increased effort to breathe by the patient.

6. The method of claim 1, wherein the method is performed during ventilation of the patient in a ventilation mode of neutrally adjusted ventilation assist.

7. The method of claim 2, further comprising:
switching between the first level and the second level of ventilatory assist by changing a NAVA level determining a proportion of ventilatory assist in relation to the bioelectric signal.

8. The method of claim 2, wherein one of the first level and second level of ventilatory assist is a level of zero ventilatory assist or a level of nearly zero ventilatory assist.

9. The method of claim 2, wherein, following a change in level of ventilatory assist, a plurality of consecutive breaths are provided to the patient at the second level of ventilatory assist, and the response in the bioelectric signal is determined based on a mean value of the bioelectric signal during the plurality of consecutive breaths.

10. The method of claim 1, further comprising:
communicating, using a notification system of the ventilation system, the determination of leakage or abnormal resistance to an operator of the breathing apparatus through generation of a visible, audible and/or tactile alarm signal.

11. A system for detection of leakage or abnormal resistance in a ventilation system, the system including a breathing apparatus configured to provide a mechanical ventilation to a patient, comprising:
a bioelectric sensor detecting a bioelectric signal indicative of the patient's effort to breathe, and
a control computer configured to receive the bioelectric signal detected by the bioelectric sensor, the control computer further configured to determine a change in the bioelectric signal received from the bioelectric sensor and to determine leakage or abnormal resistance in the ventilation system based on the change in the bioelectric signal,
wherein the bioelectric signal is at least one of an Edi signal or an EMG signal, indicative of electrical activity of the patient's respiratory muscles, or an EEG signal indicative of electrical activity of the patient's respiratory centres of a brain, and
wherein the control computer is configured to control the mechanical ventilation provided to the patient by the breathing apparatus based on the bioelectric signal.

12. The system of claim 11, wherein the control computer is configured to
control the breathing apparatus to change a level of ventilatory assist provided to the patient from a first level of ventilatory assist to a second level of ventilatory assist, the first level being different from the second level;
determine a response ($\Delta rd_{A2}$) in the bioelectric signal to the change in the level of ventilatory assist, and
determine leakage or abnormal resistance in the ventilation system based on the response in the bioelectric signal.

13. The system of claim 12, wherein the control computer is configured to
change the level of ventilatory assist from the first level of ventilatory assist to the second level of ventilatory assist;
determine a first response ($\Delta rd_{A1}$) in the bioelectric signal to the first change in the level of ventilatory assist;
then subsequently change the level of ventilatory assist from the first level of ventilatory assist to the second level of ventilatory assist;
determine a second response ($\Delta rd_{A2}$) in the bioelectric signal to the second change in the level of ventilatory assist, and
determine leakage or abnormal resistance in the ventilation system based on a comparison between the first response and the second response.

14. The system of claim 13, wherein the control computer is configured to:
determine a difference between the first response ($\Delta rd_{A1}$) and the second response ($\Delta rd_{A2}$), and
determine leakage or abnormal resistance in the ventilation system (1) when the difference between the first response and the second response exceeds a set threshold value.

15. The system of claim 11, wherein the control computer is configured to control the breathing apparatus to ventilate the patient at a substantially constant level of ventilatory assist and to determine that leakage or abnormal resistance in the ventilation system is present when the change in the bioelectric signal indicates an increased effort to breathe by the patient.

16. The system of claim 11, wherein the breathing apparatus is operated in a NAVA mode.

17. The system of claim 12, wherein the control computer is configured to automatically switch between the first level and second level of ventilatory assist by changing a NAVA level determining the proportion of ventilatory assist in relation to the bioelectric signal.

18. The system of claim 12, wherein one of the first and second levels of ventilatory assist is a level of zero ventilatory assist or a level of nearly zero ventilatory assist.

19. The system of claim 12, wherein the control computer is configured to control, following a change in the level of ventilatory assist, the breathing apparatus to deliver a plurality of consecutive breaths to the patient at the second level of ventilatory assist, and to determine the response in the bioelectric signal based on a mean value of the bioelectric signal during the plurality of consecutive breaths.

20. The system of claim 11, wherein the control computer is configured to cause the determination of leakage or abnormal resistance to be communicated to an operator of the breathing apparatus by causing a visible, audible and/or tactile alarm signal to be generated by the breathing apparatus.

21. A computer program for detection of leakage or abnormal resistance in a ventilation system, the system including a breathing apparatus configured to provide a mechanical ventilation to a patient, the computer program stored on a non-transitory computer-readable storage medium and including a set of instructions executable via a control computer of the breathing apparatus, the control computer coupled to a bioelectric sensor for detecting a bioelectric signal indicative of the patient's effort to breathe, to cause the control computer to perform the steps of claim 1.

* * * * *